United States Patent
Wang

(10) Patent No.: US 6,759,232 B2
(45) Date of Patent: Jul. 6, 2004

(54) METHOD OF FACILITATING MASS PRODUCTION AND SPORULATION OF ARBUSCULAR MYCORRHIZAL FUNGI ASEPTIC IN VITRO

(76) Inventor: Wen-Kai Wang, No.22-1, Hwa-Inn Street Chung Shan area, Taipei City (TW)

( * ) Notice: Subject to any disclaimer, the term of this patent is extended or adjusted under 35 U.S.C. 154(b) by 242 days.

(21) Appl. No.: 10/135,758

(22) Filed: Apr. 29, 2002

(65) Prior Publication Data

US 2003/0203474 A1 Oct. 30, 2003

(51) Int. Cl.⁷ .......................... C12N 1/18; C12N 1/16; C12N 1/14
(52) U.S. Cl. .................. 435/254.1; 47/1.1; 435/254.11; 435/256.8; 435/911
(58) Field of Search ......................... 435/254.1, 254.11, 435/256.8, 911; 47/1.1

(56) References Cited

U.S. PATENT DOCUMENTS

| | | | | |
|---|---|---|---|---|
| 5,554,530 A | * | 9/1996 | Fortin et al. | 435/256.8 |
| 5,786,188 A | * | 7/1998 | Lamar et al. | 435/177 |
| 6,143,549 A | * | 11/2000 | Lamar et al. | 435/242 |
| 6,576,457 B1 | * | 6/2003 | Hua | 435/256.8 |

* cited by examiner

*Primary Examiner*—Herbert J. Lilling
(74) *Attorney, Agent, or Firm*—Pro-Techtor International Services

(57) ABSTRACT

Provided is a method for the in vitro aseptic mass production and sporulation of arbuscular mycorrhizal fungi (AMF). The method comprises providing symbiotic root organs with AMF propagules and spores after the root organs are inoculated with AMF inoculums in advance to form AMF propagules in the root organs and cultivating them in an aseptic container, and then providing the whole symbiotic root organs and AMF propagules with liquid medium for a temporary contact between the liquid medium and the root organ with AMF propagules in order to cultivate AMF, then removing the liquid medium from the symbiotic root organs and arbuscular mycorrhizal fungal propagules and finally repeating former two steps periodically to facilitate the mass production and sporulation of the arbuscular mycorrhizal fungi.

15 Claims, 3 Drawing Sheets

METHOD OF FACILITATING MASS PRODUCTION AND SPORULATION OF ARBUSCULAR MYCORRHIZAL FUNGI ASEPTIC IN VITRO

BACKGROUND OF THE INVENTION

1. Field of the Invention

The present invention is relates to a method for the in vitro aseptic mass production and sporulation of arbuscular mycorrhizal fungi, especially cultivating the fungal propagules and spores by using root organs of symbiotic host plant in a limited aseptic space where liquid nutrient medium steadily floods and then drains out at regular intervals.

2. Description of Related Art

After well development of modern science and technology, the abusiveness of chemical fertilizers and pesticides in current agriculture and horticulture causes pollution and destruction of natural environment even though output of crops rises rapidly. Therefore, governments of different countries in the world all give highly regards to development and management of sustainable agriculture in recent years. And one feasible way in accord with the sustainable agricultural issues is to generalize the recyclable organic agricultural cultivation methods that are treated as the most remarkable ones. Among these methods, utilizing naturally existent plant growth prompting rhizomicrobes (PGPR) to enhance absorption of aliments and resistance against a hostile circumstance is an influential developing orientation in both of domestic and overseas researches Arbuscular mycorrhizal fungi (AMF), being a kind of beneficial symbiotic fungi, can come into symbiosis with virtually 70% of all cultivated plants by infecting their roots and colonizing invasively inside root cells, which also makes them getting the name of endomycorrhizal fungi. They are mainly characterized by their tiny, bifurcate and branched arbuscules grown in cortex cells of plant roots whereby they are named. Hyphae of fungal mycorrhizae will extend outwards from the root surface functioning as root fibrils after the mycorrhizae is grown, and thus contribute to expansion of spreading range of the root system to promote root capabilities of nutrient uptake. Mycorrhizal fungi is proofed to be a kind of microbial fertilizers due to their stimulating actions on plant growth which is confirmed by many domestic or overseas research reports. The actions include: (1) increasing absorption of microelements; (2) increasing absorption of phosphates; (3) promoting resistance of infected plants to pathogens; (4) enhancing capability of drought resistance; (5) suppressing absorption of nocuous elements; and (6) connecting with other plants via hyphae.

Accordingly, to efficiently utilize the above-mentioned microorganism can not only enhance the growth of plants but also lower opportunities of using fertilizers and agricultural chemicals to further contribute to environment protection. However, the absolute symbiosis between AMF and plants, i.e. no AMF propagules or spores have been successfully cultivated in a sterile medium without a host plant despite the large amount of domestic and overseas researches carried out to date. The most difficult reason to apply AMF as one of microorganism fertilizers is no cheaper and more efficient method that is found now to mass-produce AMF inoculums of a high quality without any adulterated microbial contaminants for commercial applications. Therefore the price is still high enough to affect the farmer willing of adopting the above-mentioned fertilizer. It will be very helpful for generalizing this excellent microbial fertilizer to know in advance how to lower the cost of using AMF inoculums.

Conventional methods to cultivate AMF propagules include as follows:

1. Potted cultivating method carried out with traditional potted plants having AMF inoculation which is easily understood from the previous description is first preparing some mycorrhizae or spores of AMF as inoculums to be inoculated into the radicle of a host plant cultivated in pots or a greenhouse and then cultivating AMF therein. However, the time required for cultivation of AMF is quite long and the product is unexpectable due to the possibility of introducing contaminants in the soil at the same time.

2. Hydroponic cultivating method is to cultivate symbiotic host plants inoculated with AMF in a specialized hydroponic device with nutrient liquid in which the host plants and AMF inoculums therein are submerged to enhance the growth of mycorrhizae and sporulation of AMF. However, though efficiency of AMF production for this method is better than the method used for potted plants, frequently refreshing the nutrient liquid is needed to prevent from serious problem of adulterated microbial contaminants. And the soaked state of the host plants and AMF therein caused by aquatic environment in this method is not the normally and naturally growth condition for AMF which results in the quantity of AMF sporulation failing to increase.

3. Aeroponic cultivating method is to cultivating symbiotic host plants inoculated with AMF in a specialized aeroponic container where vaporized nutrient liquid is provided to the plants and AMF therein. Cultivating large quantities of AMF propagules becomes possible even in the soilless situation. But the deficiencies of this method comprise the need of building a specific aeroponic container, the requirement of huge amount of vaporized nutrient liquid with necessary work to watch and refresh them, and failure to avoid the problem of adulterated microbial and pathogen contaminants.

4. Transformed root organ cultivating method uses isolated plant roots genetically transformed by the Ri plasmid of Agrobacterium rhizogenes (Tepfer, 1984, Cell, Vol. 37, 959–967) to be able to grow rapidly and independently and be inoculated with pure AMF to become a symbiotic root system (Mugnier and Mosse, 1987, Phytopathology, Vol. 77, 1045–1050). It is an advanced cultivating method to acquire AMF propagules without adulterated microbial contaminants in specialized cultivating circumstances after pure AMF are inoculated into the transformed root organ.

Mugnier et al. in U.S. Pat. No. 4,599,312 issued on Jul. 8, 1986 in the name of Rhone-Poulenc Agrochimie, Wood et al. in European Patent Application No. EP-A-209,627 published on Jan. 28, 1987, and Fortin et al. in U.S. Pat. No. 5,554,530 issued on Sep. 10, 1996 in the name of Univerfsite de Montreal all teach cultivating transformed root organs and AMF therein by adopting the solidified medium in the transformed root organ cultivating method. However, root organs have to penetrate themselves into the solidified medium used to cultivate root organs aseptic in vitro to dissolve nutrients from the solidified medium, and it is hard to the root organs for growth that the solidified medium is oxygen-poor environment. Accordingly a plane type cultivating is the only way to do because the growth of the root system is hindered by the solid medium. Comparing to the potted, hydroponic and aeroponic cultivating methods that all practice the solid type cultivating using the complete plant root system, the adoption of solidified medium is not integrally efficient enough and needs much more procedures in the regaining process by first liquefying the solidified medium and then filtering the liquefied solution to make final products. It costs high for mass production and can not proceed on a large scale.

The transformed root organ cultivating method can use liquid (solution) medium to cultivate the root system too. Three types including the submerged style, rotating drum, and the airlift style are described as followed:

The submerged style indicates cultivating transformed root organs in shallow liquid medium by still placed cultivation (Nuutila, 1995, Plant Cell Rep., Vol. 14, 505–509). In practice, the depth of the liquid nutrient medium cannot be large in order to prevent the root organs from the asphyxiant counteraction that is not good for growth. Therefore the submerged style is unable to contribute to the incremental reproduction of AMF propagules on a mass-produced scale.

Rotating drum, also called the vibrating style, indicates cultivating the root organs in a predetermined quantity of the liquid medium and adding the amount of dissolved oxygen in the solution by spinning stir or vibration. The stress caused by spinning stir and vibration will inhibit the growth of root organs and decrease the incremental reproduction rate of AMF at the same time.

The airlift style indicates cultivating root organs in a container full of liquid nutrient medium and releasing bubbles continuously from the bottom of the container to facilitate breathing of root organs (Jolicoeur, 1999, Biotechnology and Bioengineering, Vol. 63, No. 2, 224–232). The method which obviously overcomes the asphyxiant problem met in the submerged style and is free from the excess mechanical stress arising in the rotating drum style is a more feasible way in all methods adopting liquid medium. But sterile air should be injected persistently into the container, and the injection process usually costs high and allows for adulterated microbial contamination to occur. Meanwhile, both of the root organs and AMF therein are submerged continuously in the liquid medium during the process, and the liquid-full container is not a normal growth circumstance to the root organ and AMF though a large quantity of dissolved oxygen is obtainable in the container by injected air. Therefore the unit efficiency is lower than the submerged style.

In conclusion, the conventional difficulty of keeping low cost compatible with high quality of final products is always a chock point of cultivating AMF in vitro. The cheaper and lower technical methods of above-mentioned potted, hydroponic and aeroponic ones have the difficulty to control product quality and the risk of adulterated microbial contamination both discouraging farmers from being willing to adopt them. Higher quality can be maintained by using the forth method of transformed root organ which is the main worldwide struggling development. But the generalized range is limited due to the high cost of this method.

Therefore, how to overcome the problems met in the symbiotic cultivation of transformed root organs and AMF in order to lower cost, promote their production and maintain the steady quality of AMF species is in bad need and will become the main technological part to generalize this benefit microbial fertilizer.

SUMMARY OF THE INVENTION

Accordingly, one objective of the present invention is to provide a better circumstance to cultivate transformed root organs and AMF therein where effective provision of nutrients and well ventilation for oxygen are available to overcome the conventional negative influences of long-termed submergence and deficient ventilation on the root organs and AMF.

A second objective of the present invention is to provide a feasible and low-cost solution for the growth and sporulation of AMF cultivated in liquid aseptic symbiotic process by simplifying needed procedures, lowering the risk of contamination and promoting the incremental reproduction rate of AMF.

A third objective of the present invention is to provide a method which is controllable and adjustable to get the desired sporulation of AMF by changing different kinds of liquid medium or timing of the contact between AMF propagules and liquid medium to facilitate the mass production of a large amount of AMF propagules for generalizing this excellent microbial fertilizer to protect our living environment.

In order to achieve the objects set forth, a method for the in vitro aseptic mass production and sporulation of arbuscular mycorrhizal fungi is featured by providing symbiotic root organs with AMF propagules and spores after the root organs are inoculated with AMF inoculums in advance to form AMF propagules in the root organs and cultivating them in an aseptic container, and then providing the whole symbiotic root organs and AMF propagules with liquid medium for a temporary contact, then removing the liquid medium from the symbiotic root organs and arbuscular mycorrhizal fungal propagules and finally repeating former two steps periodically to facilitate the mass production and sporulation of the arbuscular mycorrhizal fungi.

Other objects, advantages and novel features of the invention will become more apparent from the following detailed description when taken in conjunction with the accompanying drawings.

BRIEF DESCRIPTION OF THE DRAWINGS AND DIAGRAMS

DETAILED DESCRIPTION OF THE INVENTION

Figure 1:
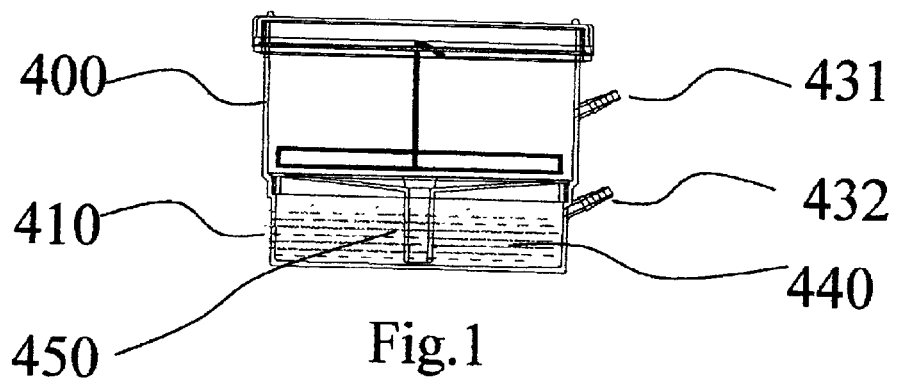
FIG. 1–FIG. 4 is a schematic flow chart showing equipments and cultivating procedures for a first preferred embodiment of the method in accordance with the present invention.

Reference will now be made to the drawing figure to describe the present invention in detail.

The present invention is relates to a method for the in vitro aseptic mass production and sporulation of arbuscular mycorrhizal fungi (AMF). The method includes following steps. First, provides symbiotic root organs with AMF propagules and spores and cultivates them in an aseptic container. The symbiotic root organs are preferred to be a plant root organ attached to a hypocotyl to form root-hypocotyl explants or transformed by infecting with a bacterium containing a root-inducing plasmid or a tumor-inducing plasmid. Besides, the root organs are preferred to be one in the group consisting of *Dacus carota, Nicotian tabacum, Medicago savita, Tagetes erecta, Chrysanthemum coronarium, Ipomoea reptans, Lycopersicon esculentum, Luffa cylindrica* and *Carica papaya*. The selected plant root organs are inoculated with AMF inoculums in advance to cultivate the root organs and AMF symbiotically forming AMF propagules in the root organs. The inoculated AMF is usually selected from the group consisting of *Glomus intraradices, Glomus mosseae, Glomus etunicatum, Glomus occultum, Gigaspora margarita, Acaulospora morrowiae, Acaulospora scrobiculata* and *Entrophospora kentinensis*. Second, providing the whole symbiotic root organs and AMF propagules with liquid medium for a temporary contact. Third, removes the liquid medium from the symbiotic root organs and arbuscular mycorrhizal fungal propagules after they are cultivated by the liquid medium. Finally, repeats former two steps periodically to facilitate the mass production and sporulation of the arbuscular mycorrhizal fungi.

The method in accordance of the present invention can be proceeded in any kind of reactors, such as pouring style reactors (Shinsaku Takayama & Motomu Akita, Plant Cell, Tissue and organ Culture 39:147–156, 1994) and spraying style reactors (Seung Han Woo, et al., J. Chem. Tech. Biotechnol. 66, P355–362, 1996). The other containers shown in Taiwan Patent Publication No. 336881 "Pneumatic Bio-reactor" and PCT Patent Publication No. WO96/25484 "In Vitro Culture Container", and the nutrient mist type bioreactor "Mistifier" made by Manostat Corporation can also be used for the method.

Figure 2:
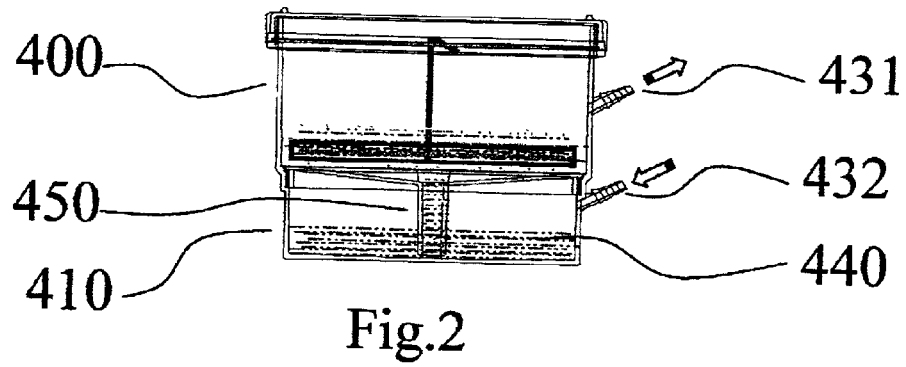
Figure 3:
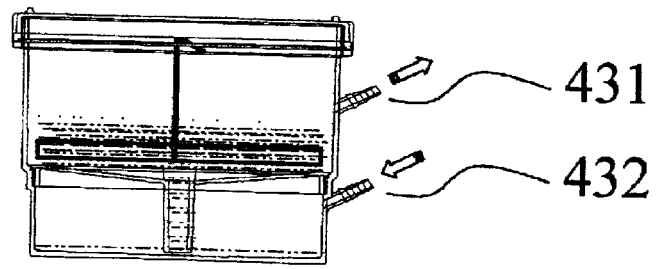
Figure 4:
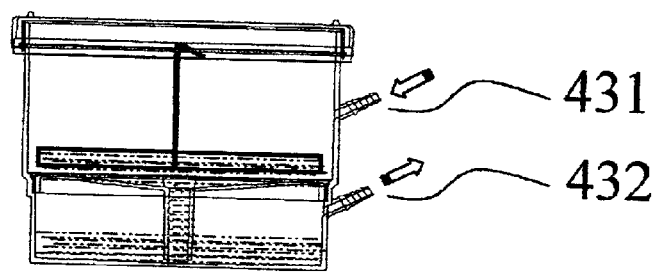

Referring to FIG. 1 to FIG. 4, a preferred embodiment of the method in accordance with the present invention is introduced. First, in FIG. 1, a transformed root organ is placed in an aseptic container 400 and is inoculated with AMF inoculums to be cultivated in a symbiotic status. Liquid nutrient medium 440 is in advance poured into a reservoir 410 mounted to the bottom of the container 400 with a join tube 450 connecting and transporting liquid nutrient medium 440 therebetween. Meanwhile, a first air vent 431 and second air vent 432 with ducts connected thereto are disposed in the container 400 and the reservoir 410 respectively to adjust the air pressure therein. In succession, as shown in FIG. 2, an air pressure difference is established gradually by either extracting air from the container 400 via the air vent 431 to lower air pressure therein or charging air into the reservoir 410 via the vent 432 to increase the air pressure therein, even or changing the air pressure of the container 400 and reservoir 410 at the same time. The liquid nutrient medium 440 reserved in the reservoir 410 will be forced to move to the container 400 via the tube 450 by the increasing air pressure difference till the whole symbiotic root organ and AMF propagules is submerged in the poured liquid nutrient medium 440 or the reservoir 410 is empty, as shown in FIG. 3. After a predetermined submerging period, as shown in FIG. 4, stops air pumping to discharge the container 400 or charge the reservoir 410 and makes the air pressure difference lowering naturally. The liquid nutrient medium 440 used to cultivate the AMF propagules will flow back to the reservoir 410 due to its own weight. The feature of this embodiment is the air pressure difference between the container 400 and reservoir 410 can be easily and repeatedly established or eliminated to move the liquid medium 440 from one of the container 400 and reservoir 410 to the other by pumping air in one or both of the container 400 and reservoir 410. In this arrangement, the root organ and AMF propagules can be cultivated better because they get enough nutrients from the liquid medium 440 in their submerged status and are free to get enough oxygen periodically in their exposed status.

Figure 5:
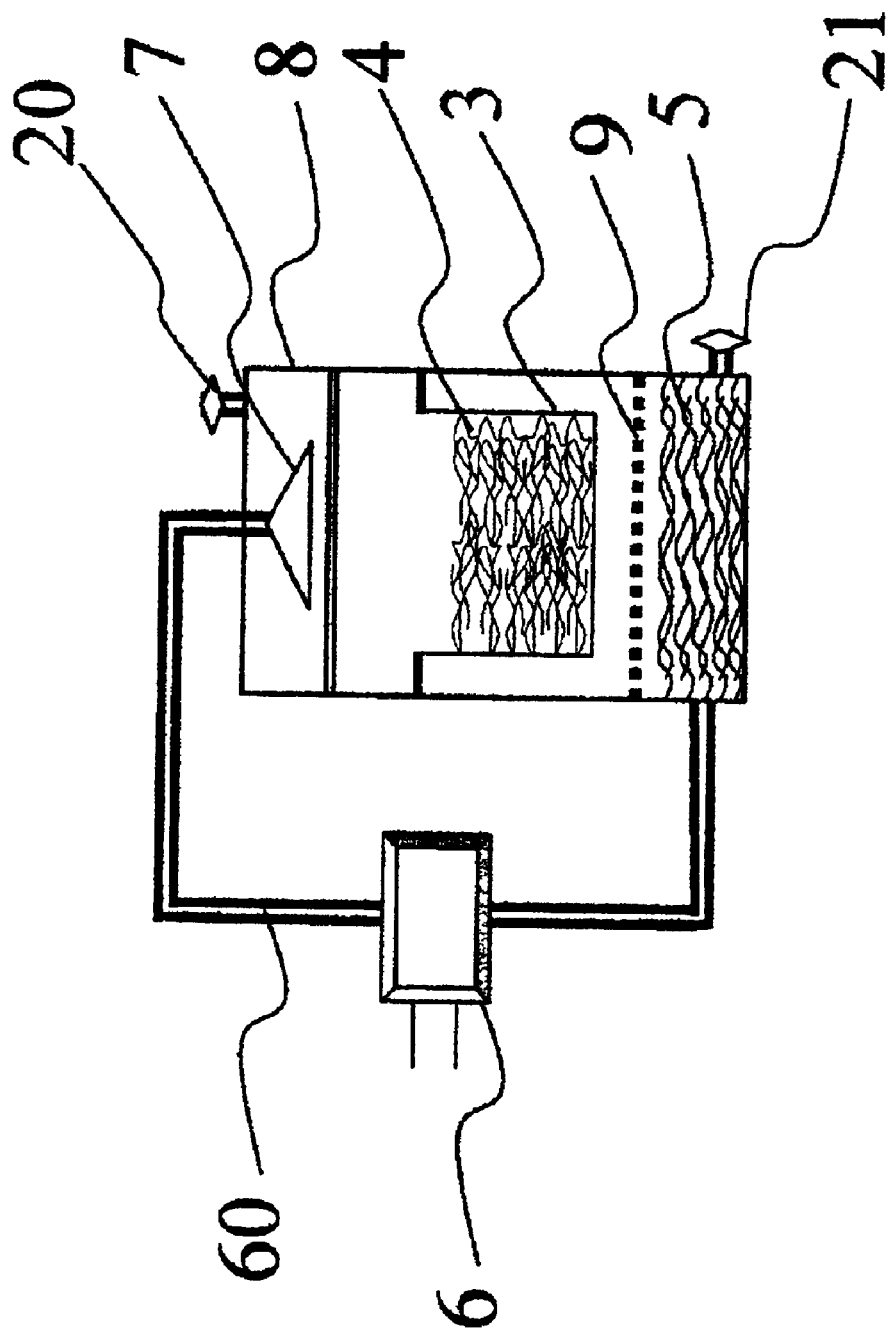
FIG. 5 is a schematic sectional view showing necessary equipments for a second preferred embodiment of the method in accordance with the present invention.

Besides, a second preferred embodiment of the method in accordance with the present invention is introduced referring to FIG. 5. The equipments used in this embodiment include a sterile container 8 having liquid nutrient medium 5. A partition 9 is disposed within the container 8 with distributed holes penetrated therethrough. And a join tube 60 having a pump 6 disposed thereon is connected to the bottom of the container 8 and a distributor 7 disposed at the top of the container 8. Thereby liquid nutrient medium 5 reserved in the container 8 can be pumped into the distributor 7 which can then sprinkle liquid nutrient medium slowly and equally over the symbiotic root organ and AMF propagules 4 cultivated in the container 8. Furthermore, two openings 20, 21 with a valve tube are disposed on one selected sidewall of the container 8 to facilitate the exchange of air or liquid medium. Obviously, in this embodiment, the symbiotic root organs and AMF propagules 4 can be cultivated in an inner tank 3 full with apertures on its sidewalls and bottom wall which disposed right under the distributor 7. The liquid nutrient medium 5 is pumped from the bottom of the container 8 to the distributor 7 via the join tube 60 and is distributively sprinkled over the root organ and AMF propagules 4. After the symbiotic root organs and AMF propagules 4 acquire continuously nutrients from the liquid medium flowing through their skin surface, some tiny and temporarily reserved liquid medium may flow through holes of the inner tank 3 and partition 9 in turn back to the container 8 due to their own weight and wait for the next possible pumping. The necessary nutrients and air used to cultivate the symbiotic AMF and root organs 4 are properly and adequately provided by regularly repeating the pumping-and-sprinkling process for a predetermined time.

The root organs and AMF propagules in the following examples are prepared by those steps introduced hereinafter.

Transformed root organ is induced by using *N. tabacum* cv. *xanthi*, one of Solanaceae, and is available after proceed following steps. First, get purebred cultivated Agrobacterium rhizogenes (CCRC 15011, Culture Collection And Research Center, Food Industry Research and Development Institute in Taiwan) and have them immersed in LB liquid medium (10 g/l of Tryptone, 5 g/l of Yeast Extract, and 2 g/l of NaCl). And then oscillate them at the speed of 150 RPM when them are cultivated at 28° C. for 40 hours until they are qualified to use when the growth index $OD_{600}$ equals to 0.8.

Second, get sterilized seeds of *N. tabacum* cv. *xanthi*, which are immersed in a 70% alcoholic solution for 30 seconds and moved to 1% sodium hypochlorite solution for 10 minutes in succession and finally cleaned twice by aseptic water, plant them on an MS pH 5.7 agar (0.8%) medium consisting of 2% of sucrose (Murashige and Skoog, 1962, Physiol. Plant v. 15, P473–479), and finally cultivate the seeds in the conditions of 26° C., 2500 lux and D/N: 16/8 hours. The seeds will grow to become a suitable useful material for other steps after 45 days.

Third, use a scalpel to dip some bacteria liquid from the cultivating medium prepared in the first step and use this scalpel cut *tabacum* stem portion prepared in the second step into several pieces to have each is about 0.8 cm, and it should be avoided for use in some of the bud portions of stem portion. Then put these stem pieces on MS agar medium consisting of 2% sucrose to cultivate them darkly at 25° C. for 48 hours to transfer hereditary substances of Agrobacterium rhizogenes to the gene of plant cell sets.

Forth, remove infected stem pieces from the medium after co-culture for 40 hours, and clean them up under an aseptic condition by using MS liquid medium consisting of 500 mg/l cefotaxime to get rid of newly germinated Agrobacterium rhizogenes. After suck residual medium on the stem pieces by filter paper, cultivate these stem pieces darkly at 26° C. on an MS agar medium consisting of 500 mg/l cefotaxime and 2% sucrose. The needed fibrous roots will germinate and grow in 2 to 3 weeks and can be confirmed by the hue gender of ammoniacal silver nitrate comparing to opines (Petit et al., 1983, Mol. Genet., vol. 190, P204–214).

Finally, cut aseptically off some of the fibrous roots which is in better growing conditions in the forth step and cultivate continuously some of stem pieces containing no *tabacum* tissues on an MS agar medium with 2% sucrose but without antibiotics like cefotaxime to retain proliferation of fibrous roots. Fibrous roots having no Agrobacterium rhizogenes remain and growing well and fast are selected to provide as sources of pure-line subculture for future uses.

In the arbuscular mycorrhizal fungi aspect, several known kinds of arbuscular mycorrhizal fungi are basically able to be used as inoculums in accordance with the present invention, including fungi of Glomus sp., Gigaspora sp., Acaulospora sp., Entrophospora, and Sclerocystis sp. The spore inoculums can be obtained from soil sifting by following steps.

First, get an appropriate quantity of soil containing AMF and have it suspended in a large amount of water. After 10 seconds, get upper-layered liquid to be filtrated by sieves used in a sequence of the size of their sieve pores (from a largest one to a finest one as following: 250 $\mu$m→125 $\mu$m→60 $\mu$m→37 $\mu$m).

Then, move siftings to a centrifuge tube and add some water therein, and then centrifuge them in the speed of 800 xg for 2 minutes. Leave precipitates in the tube after remove off upper clear liquid therein.

Third, have the precipitates suspended in 40% sucrose solution, and then centrifuge them in the speed of 800 xg for 2 minutes. Spores are acquired in a sieve when use the sieve to strain the centrifuged upper clear liquid.

Forth, classify roughly the gained spores by their appearing colors and sanitize them with sterilizer solution (Becard & Fortin, 1988, New Phytol. Vol. 108, P211–218). In this process, first clean the spores twice with 2% chloramines T, and then clean them five times with aseptic solutions consisting of 1% streptomycin and 0.5% gentamycin. The spores can be refrigerated at 4° C. before they serve.

Figure 6:
FIG. 6 is a photograph taken with a photon microscope showing hyphae of arbuscular mycorrhizal fungi winding gradually the transformed root organs.
Figure 7:
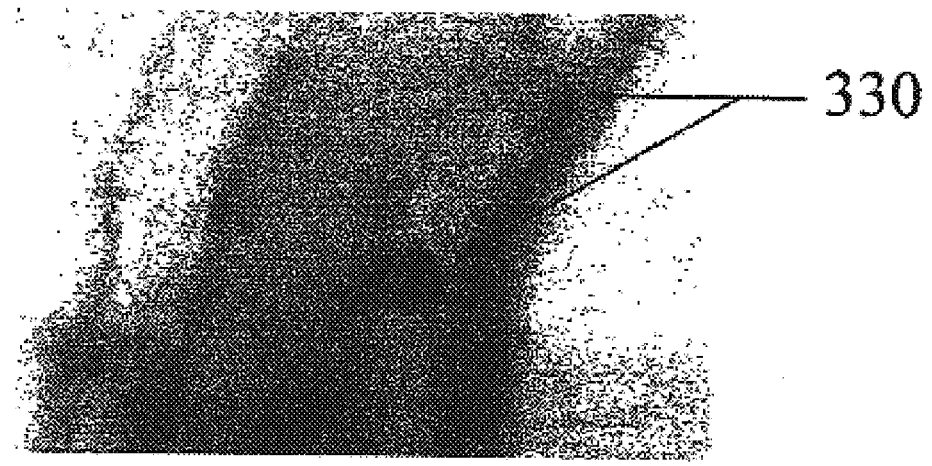
FIG. 7 is a photograph taken with a photon microscope showing AMF arbuscules growing in the root organ.

Fifth, take single sterilized spore and place it in 1.5% w/v water agar to germinate and grow. Pick some of AMF, which is in a well growing condition and has no introduced contaminant therewith, and have them being cut off with agar to be placed with the pure line subculture root organs provided as mentioned above. In 27° C. dark cultivation, hyphae of AMF will infect its neighboring root organ automatically. The colonization of AMF onto the root organs can be observed after the tissue of root organ is dyed by aniline blue (AMF Application Technical Handbook publish, P155–156) within two or three weeks. Referring to FIGS. 3 to 5, hyphae of AMF 320 winding around root organs 310 is shown in FIG. 6. AMF arbuscules 330 growing in the root organ 310 can be observed as shown in FIG. 7. Finally, the symbiotic propagules of AMF and root organs can be used as AMF inoculums and can proceed in the cultivation of pure line subculture as the root organs.

A series of comparative tests are taken to approve the effectiveness and efficiency of the method introduced for the in vitro aseptic mass production and sporulation of arbuscular mycorrhizal fungi in accordance with the present invention. The first preferred embodiment of the method is adopted in one of the test as a comparable example hereinafter.

[Test 1: The Germination and Cultivation of Root Organs]

Prepare *tabacum* transformed root organs as mentioned above, a ventilative submerging cultivation container with an aerator and MS pH 5.7 liquid medium consisting of 2% sucrose for the test. And then cultivate the root organs by proceeding the following steps:

1. Place 240 ml of liquid medium in the container, and have it sterilized under high temperature and pressure (121° C., 1.2 kg/cm$^2$) for 20 minutes. Cool down the liquid medium before it serves.
2. Under an aseptic condition, open the upper cover of the container to place well-grown root organs therein, whose fresh weight is about 1 g (0.065 g of dry weight, which is weighed after the root organ is dried at 80° C. for 8 hours) in an inner disk of the container before close the cover of the container.
3. In the dark circumstance, begin to submerge the root organs at 26° C. for 5 minutes at a regular interval of three hours to cultivate them periodically after connect the container to the working aerator.
4. Measure the proliferation of the root organs after cultivate the root organ for one month and two months respectively. The method for measuring is first taking out the root organ from the container under the aseptic condition, using filter paper to suck residual medium from the root organ sufficiently, weighing the root organ placed in an aseptic Petri dish and finally moving the root organ back to inside of the container.

The test result is shown in the following table comparing with a contrast experiment using the method of the vibrating style describing above as a related art.

|  | Increasing rate of fresh weight for the first month | Increasing rate of fresh weight for the second month | Increasing rate of dry weight for two months |
|---|---|---|---|
| Method of the invention | 5.28 ± 0.52 | 4.33 ± 0.66 | 20.7 ± 0.57 |
| Vibrating style of prior art | 4.13 ± 0.67 | 3.55 ± 0.83 | 12.7 ± 0.74 |

[Test 2: The Symbiotic Cultivation and Sporulation of AMF]

Prepare symbiotic transformed root organs and AMF propagules (*Glomus intraradices*) as mentioned above, a ventilative submerging cultivation container with an aerator and Minimal pH 5.7 liquid medium consisting of 1% sucrose (Becard and Fortin, 1988, New Phytol. Vol. 108, P211–218). And then cultivate the symbiotic root organs and AMF by proceeding the following steps:

1. Same as the first step in test 1.
2. Under an aseptic condition, open the upper cover of the container to place well-symbiosis AMF propagules therein, whose fresh weight is about 1.5 g (0.1 g of dry weight) in an inner disk of the container before close the cover of the container.
3. In the dark circumstance, begin to submerge the AMF propagules at 26° C. for 5 minutes at a regular interval of three hours to cultivate them periodically after connect the container to the working aerator.
4. Measure the sporulation of AMF after cultivate the root organ for two months. The method for measuring is first taking out the root organ from the container under the aseptic condition, then have them crushed within 500 ml pure water by juice machine at the speed of 30 round/sec for 30 seconds, and finally get some of the suspending solution in the juice machine to calculate the amount of AMF spores under the microscope.

The test result is shown in the following table comparing with a contrast experiment using the method of the vibrating style describing above as a related art.

|  | Proliferation amount of AMF spores |
| --- | --- |
| Method of the invention | 48300 + 6180/g-l |
| Vibrating style of prior art | 12480 + 2580/g-l |

Remark:
"g" represents the initial weight of symbiotic root organ and AMF.
"l" represents the liquid medium in liter.

Obviously, the method in accordance with the present invention benefits growth of the root organs and AMF propagules and sporulation of AMF according to the preceding testing results. The main objective or advantage of the invention is able to facilitate better growth speed of plant root organs and AMF by adopting the method comprising pour in and drain out liquid nutrient medium within any bio-reactor containers periodically. Therefore, the conventional defects of long-termed submerging and asphyxiant problem in prior arts can be overcome. The method of the present invention is much more economical and can be used to mass produce AMF propagules and spores aseptic in vitro.

It is to be understood, however, that even though numerous characteristics and advantages of the present invention have been set forth in the foregoing description, together with details of the method and function of the invention, the disclosure is illustrative only, and changes may be made in detail, especially in matters of ingredient, material, and arrangement of steps within the principles of the invention to the full extent indicated by the broad general meaning of the terms in which the appended claims are expressed.

What is claimed is:

1. A method for mass production and sporulation of arbuscular mycorrhizal fungi aseptic in vitro in a container comprising:
    providing symbiotic root organs with arbuscular mycorrhizal fungal propagules growth in vitro autonomously;
    providing a liquid medium for a temporary contact with the symbiotic root organs and arbuscular mycorrhizal fungal propagules and is suitable for the symbiotic root organs and arbuscular mycorrhizal fungal propagules growth;
    removing the liquid medium from the aseptic in vitro after the symbiotic root organs and arbuscular mycorrhizal fungal propagules cultivated by the liquid medium between whiles; and
    repeating former two steps periodically to facilitate the mass production and sporulation of the arbuscular mycorrhizal fungi.

2. The method as recited in claim 1, wherein the symbiotic root organs and arbuscular mycorrhizal fungal propagules cultivated in an aseptic container and reserved the liquid medium in the same container or different container.

3. The method as recited in claim 2, wherein the symbiotic root organs and arbuscular mycorrhizal fungal propagules and the liquid medium located in the same container which have two-compartment within, wherein the symbiotic root organs and arbuscular mycorrhizal fungal propagules located on the upper compartment, the liquid medium reserved on the lower compartment.

4. The method as recited in claim 3, wherein further comprising: a join tube disposed between and connection the two-compartment of the aseptic container for the liquid medium capable of passing through the two-compartment.

5. The method as recited in claim 3, wherein further comprising a first air vent disposed the aseptic container where is near the symbiotic root organs and arbuscular mycorrhizal fungal propagules and a second air vent disposed the aseptic container where is near the liquid medium, thereby an air pressure difference is established via the first and second vents to force the liquid medium moving to the root organ located space and having the symbiotic root organs and arbuscular mycorrhizal fungal propagules submerged therein for a predetermined period, and the liquid medium is then flowing back to said reserved space by adjusting the air pressure difference.

6. The method as recited in claim 2, wherein the symbiotic root organs and arbuscular mycorrhizal fungal propagules and the liquid medium located in the same container, wherein the symbiotic root organs and arbuscular mycorrhizal fungal is placed on the vessel and which disposed within the upper of aseptic container, the liquid medium reserved on the lower of aseptic container.

7. The method as recited in claim 6, wherein a join tube disposed on the outer of the aseptic container and further having a pump disposed between and joining the upper and lower of the aseptic container, thereby the liquid medium pumped to the upside of the aseptic container and sprinkled over the symbiotic root organs and arbuscular mycorrhizal fungal propagules to cultivate them.

8. The method as recited in claim 7, wherein further comprising: a distributor disposed on one end of the join tube and located above the root organs to be used to sprinkle the liquid medium.

9. The method as recited in claim 8, wherein further comprising a partition located within the compartment where disposed the symbiotic root organs and arbuscular mycorrhizal fungal propagules, and having a several holes thereon for providing the liquid medium passing through the compartment, so as to contact with the symbiotic root organs and arbuscular mycorrhizal fungal propagules.

10. The method as recited in claim 1, wherein the symbiotic root organ is a transformed root organ infected by bacteria with root-inducing plasmids.

11. The method as recited in claim 1, wherein the symbiotic root organ is a transformed root organ infected by bacteria with tumor-inducing plasmids.

12. The method as recited in claim 1, wherein the root organ is selected from the group consisting of Apiaceae, Solanaceae, Leguminosae, Asteraceae, Cucurbitaceae, Caricaceae and Convolvulaceae.

13. The method as recited in claim 1, wherein the root organ is selected one of the group which composing *Dacus carota, Nicotian tabacum, Medicago savita, Tagetes erecta, Chrysanthemum coronarium, Ipomoea reptans, Lycopersicon esculentum, Luffa cylindrica* and *Carica papaya*.

14. The method as recited in claim 1, wherein the arbuscular mycorrhizal fungus is selected one of the group which composing Gigasporaceae, Glomaceae and Acaulosporaceae.

15. The method as recited in claim 1, wherein the arbuscular mycorrhizal fungus is selected one of the group which composing *Glomus intraradices, Glomus mosseae, Glomus etunicatum, Glomus occultum, Gigaspora margarita, Acaulospora morrowiae, Acaulospora scrobiculata* and *Entrophospora kentinensis*.

* * * * *